US012729392B2

(12) United States Patent
Kim et al.

(10) Patent No.: US 12,729,392 B2
(45) Date of Patent: Sep. 8, 2026

(54) BIOMARKER COMPOSITION FOR PREDICTING PROGNOSIS OF BRAIN DISEASE CAUSED BY MICROPLASTIC EXPOSURE AND METHOD FOR PREDICTING PROGNOSIS USING SAME

(71) Applicant: KOREA INSTITUTE OF RADIOLOGICAL & MEDICAL SCIENCES, Seoul (KR)

(72) Inventors: Jin Su Kim, Seoul (KR); Hyeongi Kim, Chungju-si (KR); Javeria Zaheer, Cheongju-si (KR); Yong Jin Lee, Seoul (KR); Kyung Jun Kang, Seoul (KR); In Ok Ko, Yangju-si (KR)

(73) Assignee: KOREA INSTITUTE OF RADIOLOGICAL & MEDICAL SCIENCES, Seoul (KR)

( * ) Notice: Subject to any disclaimer, the term of this patent is extended or adjusted under 35 U.S.C. 154(b) by 416 days.

(21) Appl. No.: 17/927,714

(22) PCT Filed: Jul. 5, 2021

(86) PCT No.: PCT/KR2021/008493
§ 371 (c)(1),
(2) Date: Nov. 24, 2022

(87) PCT Pub. No.: WO2022/010202
PCT Pub. Date: Jan. 13, 2022

(65) Prior Publication Data

US 2023/0212637 A1 Jul. 6, 2023

(30) Foreign Application Priority Data

Jul. 7, 2020 (KR) ........................ 10-2020-0083403

(51) Int. Cl.
*C12Q 1/02* (2006.01)

(52) U.S. Cl.
CPC ..................................... *C12Q 1/02* (2013.01)

(58) Field of Classification Search
CPC ................................. C12Q 1/02; C12Q 1/689
See application file for complete search history.

(56) References Cited

U.S. PATENT DOCUMENTS

| | | | |
|---|---|---|---|
| 2006/0062774 | A1 | 3/2006 | Davis et al. |
| 2021/0121505 | A1 | 4/2021 | Nandakumar et al. |
| 2022/0096566 | A1 | 3/2022 | Bry et al. |

FOREIGN PATENT DOCUMENTS

| | | | |
|---|---|---|---|
| KR | 10-2000-0006190 | A | 1/2000 |
| WO | 2017-079450 | A1 | 5/2017 |
| WO | 2019-169160 | A1 | 9/2019 |
| WO | 2020-106983 | A1 | 5/2020 |

OTHER PUBLICATIONS

Li et al. "Polyethylene microplastics affect the distribution of gut microbiota and inflammation development in mice" Chemosphere 244 (2020) 125492, 10 pages, published online Nov. 27, 2019 (Year: 2020).*

Li et al. "Polyethylene microplastics affect the distribution of gut microbiota and inflammation development in mice" Chemosphere 244 (2020) 125492, 10 pages, Available online Nov. 27, 2019 (Year: 2020).*

Meiling Zhang et al., "Structural shifts of mucosa-associated lactobacilli and Clostridium leptum subgroup in patients with ulcerative colitis", Journal of Clinical Microbiology, Feb. 2007, vol. 45, No. 2, pp. 496-500.

Joana Correia Prata et al., "Environmental exposure to microplastics: An overview on possible human health effects", Journal of Clinical Microbiology, Science of The Total Environment, vol. 702, Feb. 1, 2020, 134455.

Jonathan A Hollander et al., "Beyond the looking glass: recent advances in understanding the impact of environmental exposures on neuropsychiatric disease", Neuropsychopharmacology, .Jun. 2020, vol. 45, No. 7, pp. 1086-1096.

International Search Report for PCT/KR2021/008493 mailed Oct. 21, 2021 from Korean Intellectual Property Office.

Javurek, A. B. et al., "Effects of exposure to bisphenol A and ethinyl estradiol on the gut microbiota of parents and their offspring in a rodent model", Gut Microbes, 2016, vol. 7, No. 6, pp. 471-485.

Stein, T. P. et al., "Bisphenol A Exposure in Children With Autism Spectmm Disorders", Autism Research, 2015, vol. 3, pp. 272-283.

Ming, X. et al., "Metabolic Perturbance in Autism Spectmm Disorders: A Metabolomics Study", Journal of Proteome Research, 2012, vol. 11, pp. 5856-5862.

Lutkenhoff, Es et al., "Proton MRS in twin pairs discordant for schizophrenia", Molecular Psychiatry, 2010, vol. 15, pp. 308-318.

Jin, Y. et al., "Impacts of polystyrene microplastic on the gut barrier, microbiota and metabolism of mice", Science of the Total Environment, 2019, vol. 649, pp. 308-317.

Prust, M. et al., "The plastic brain: neurotoxicity of microand nanoplastics", Particle and Fibre Toxicology, 2020, vol. 17, 24, inner pp. 1-16.

De Thede, C.G.M. et al., "Altered gut microbiota and activity in a murine model of autism spectmm disorders", Brain, Behavior, and Immunity. 2014, vol. 37, pp. 197-206.

(Continued)

*Primary Examiner* — Thane Underdahl
(74) *Attorney, Agent, or Firm* — Revolution IP, PLLC

(57) ABSTRACT

The present invention relates to: a biomarker composition for predicting the prognosis of brain disease caused by microplastic exposure; and a use thereof. More particularly, it was confirmed that polyethylene microspheres (PS) in a mouse animal model orally administered with the PS penetrate brain tissue to change the level of metabolites inside the brain tissue and the diversity of intestinal microorganisms, thereby causing brain disease, and thus the present invention is intended to provide a biomarker composition for predicting the prognosis of brain disease caused by microplastic exposure, and a method for predicting the prognosis of brain disease using same.

4 Claims, 6 Drawing Sheets

(56) References Cited

OTHER PUBLICATIONS

Rosenfeld, C. S., "Microbiome Disturbances and Autism Spectmm Disorders", Dmg Metabolism and Disposition, 2015, vol. 43, pp. 1557-1571.
Kaidanovich-Beilin et al., "Assessment of Social Interaction Behaviors", Journal of Visualized Experiments, Feb. 2011, vol. 48, e2473, p. 1-6.
Florence I. Roullet et al., "Mouse Models of Autism: Testing Hypotheses About Molecular Mechanisms", Current Topics in Behavioral Neurosciences 7(1):187-212, DOI:10.1007/7854_2010_113.
Mariana Angoa-Pérez et al., "Marble Burying and Nestlet Shredding as Tests of Repetitive, Compulsive-like Behaviors in Mice", Journal of Visualized Experiments 24(82), DOI:10.3791/50978.
Francesco Strati et al., "New evidences on the altered gut microbiota in autism spectrum disorders", Microbiome. Biomed Central Ltd. London. UK vol. 5, No. 1, Feb. 22, 2017 (Feb. 22, 2017), pp. 1-11, XP021242477, DO1: 10.1186/S40168-017-0242-1.
Song Yuli et al., "Real-Time PCR Quantitation of Clostridia in Feces of Autistic Children" Applied and Environmental Microbiology vol. 70, No. 11, Nov. 1, 2004 (Nov. 1, 2004), pp. 6459-6465, XP093286193, US ISSN: 0099-2240, DO1: 10.1128/AEM.70.11.6459-6465.2004.

* cited by examiner

Prefrontal cortex– 1W

Prefrontal cortex– 1W
Cr+PCr normalization data

Hippocampus – 1W

Hippocampus – 1W
Cr+PCr normalization data

BIOMARKER COMPOSITION FOR PREDICTING PROGNOSIS OF BRAIN DISEASE CAUSED BY MICROPLASTIC EXPOSURE AND METHOD FOR PREDICTING PROGNOSIS USING SAME

TECHNICAL FIELD

The present disclosure relates to a biomarker composition for predicting the prognosis of a brain disease induced by microplastic exposure and a use thereof.

BACKGROUND ART

Autism is a neurodevelopmental disorder that impairs the ability to communicate and understand social interactions. The cause of symptom thereof is not yet clear, but some researchers speculate that it is a genetic developmental disorder, not an emotional cause. The incidence rate is 1 in 1000, and the male to female ratio is about 4:1 in the United States. According to a survey conducted in 2011, the prevalence rate of autism in Korea is over 2%, which is drawing attention. Autism is generally referred to as 'autism spectrum disorder' (ASD), which is divided into three categories in academic circles.

First category is autism for children (Kanner's Syndrome) defined by Leo Kanner, second one is Asperger's syndrome as discussed by Hans Asperger, and the last one is high functional autism including savant syndrome.

Growing babies typically show social activities such as staring at people, paying attention to voices, clenching fingers, and smiling. Babies with autism, however, dislike face-to-face contact and have great difficulty in understanding interactions in human society. When it comes to communication, the average babies say words in around their first birthday and show behaviors such as responding to the calling of their names and pointing with fingers at a toy they want, whereas babies with autism choose a different path in their communication development. Some remain silent throughout the life despite sufficient literacy skills, but prefer other methods such as drawing or sign language instead.

In relation to the cause of autism, there was a theory that it was acquired in the early stages, but now it is predominant that it is congenital. Brain structure abnormalities, genetic defects, and neurotransmitter abnormalities are usually blamed for the cause. In addition, fetal alcohol syndrome, of which children are adversely affected by pregnant mothers who like to drink alcohol, was also pointed out as a cause. However, the exact causal factor is still controversial.

Although plastic has made great contribution to the affluent daily life of modern people and industrial development owing to excellent functions and low price, it has been reported that the discarded plastic decomposes over time into pieces of microscopic sizes that are difficult to visually identify to be a cause polluting the environment and threatening human health, and the effect of microplastics on brain diseases has not been studied.

DISCLOSURE OF THE DISCLOSURE

Technical Goals

An object of the present disclosure is to provide a biomarker composition for predicting prognosis of a brain disease induced by microplastic exposure and a method for predicting the prognosis of a brain disease using the same.

Technical Solutions

The present disclosure provides a biomarker composition for predicting prognosis of a brain disease induced by microplastic exposure, including an intestinal microorganism as an active ingredient.

The present disclosure provides a method for predicting prognosis of a brain disease induced by microplastic exposure, including obtaining a sample isolated from a subject exposed to microplastic;

identifying whether ecology changes in the microorganisms and a change in a metabolite level in the sample; and comparing with a control group.

In addition, the present disclosure provides a method of providing information for predicting prognosis of a brain disease induced by microplastic exposure, including examining whether ecology changes in microorganisms and a change in a metabolite level from a sample isolated from a specimen.

ADVANTAGEOUS EFFECTS

According to the present disclosure, in a mouse animal model into which polyethylene microspheres (PS) were orally administered, since it was found that PS induced a brain disease by penetrating the brain tissue, changing the metabolite level in the brain tissue, and changing the intestinal microbial diversity, an object of the present disclosure is to provide a biomarker composition for identifying the level of various changes in the body of a subject suspected of PS exposure and predicting the prognosis of a brain disease induced by microplastic, and a method for predicting the prognosis of a brain disease using the same.

BRIEF DESCRIPTION OF DRAWINGS

FIG. 1 also shows a result of identifying the change in intestinal microbial diversity after exposure to polyethylene microspheres by performing cladogram analysis and cluster analysis.

BEST MODE FOR CARRYING OUT THE INVENTION

Figure 1:
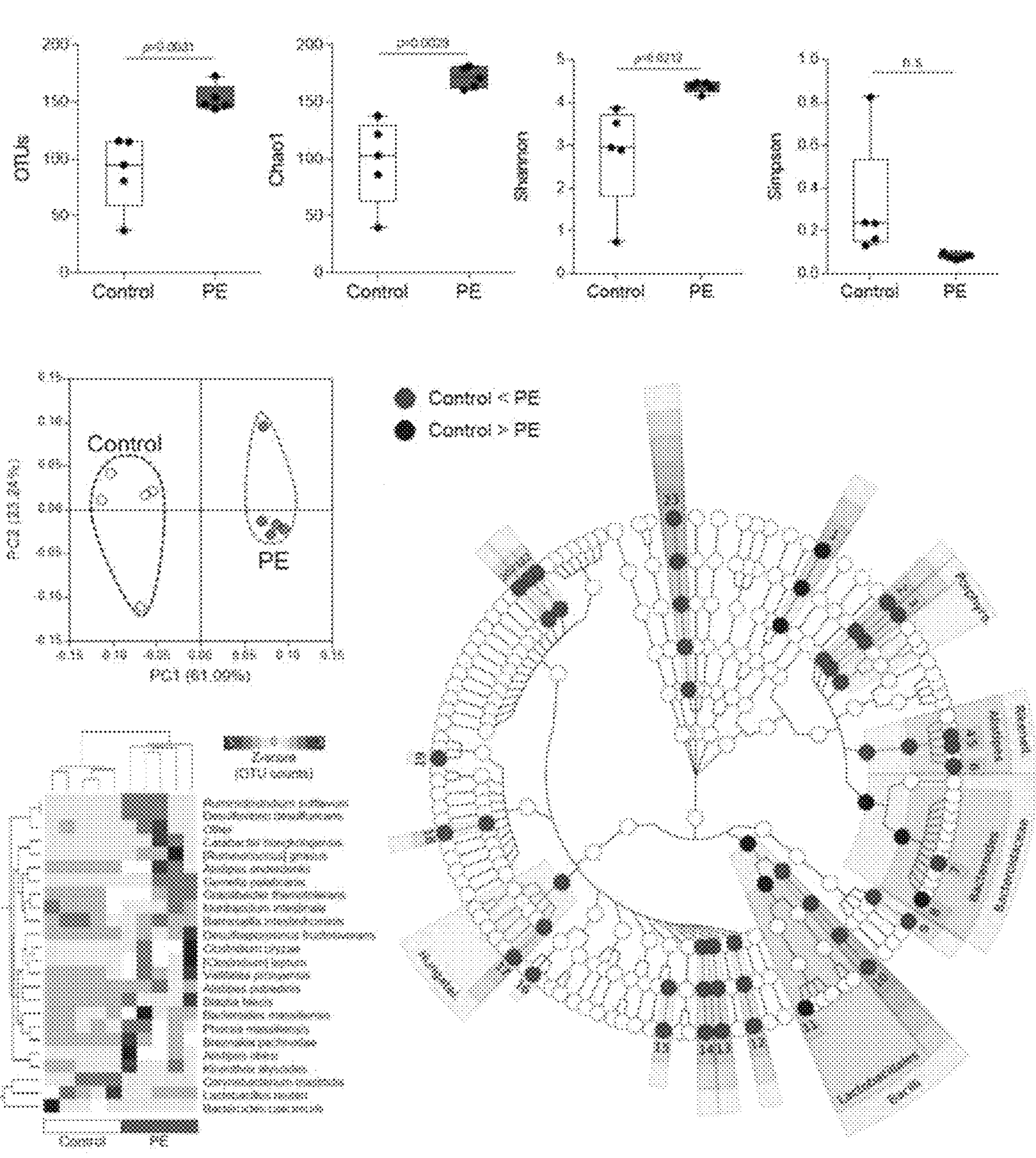
FIG. 1 shows results of alpha-diversity analysis using OTU counts, Chaol index, Shannon index, and Simpson index for 16S rRNA sequence analysis of mouse feces exposed to polyethylene microspheres, identifying the change in the diversity of the intestinal microflora by conducting a beta diversity analysis using Principal coordinates analysis (PCoA) of unweighted UniFrac method.

Hereinafter, the present disclosure will be described in more detail.

Since microplastics with a diameter of less than 5 mm are recognized as a new risk factor threatening environment and human health, the inventors of the present disclosure have found, in the course of studying the risk that may exist when polystyrene microspheres (PS), a type of microplastics, are ingested in vivo, that PS absorbed in vivo penetrated into the brain tissue or changed intestinal microbial environment to induce a brain disease, such that the inventors completed the present disclosure to provide a biomarker composition for predicting the prognosis of a brain diseases induced by microplastics by identifying the level of various biological changes induced by PS exposure.

An object of the present disclosure is to provide a biomarker composition for predicting prognosis of a brain disease induced by microplastic exposure, including intestinal microorganisms as an active ingredient.

More specifically, the intestinal microorganisms may be one or more selected from the group consisting of *Breznakia pachnodae, Gracilibacter thermotolerans, Blautia faecis, Desulfosporosinus fructosivorans, Alistipes onderdonkii, Alistipes obesi, Clostridium leptum, Clostridium oryzae, Catabacter hongkongensis, Gemella palaticanis, Ruminiclostridium sufflavum, Desulfovibrio desulfuricans*, and *Ruminococcus gnavus*.

In addition the biomarker composition may further include *Muribaculum intenstinale, Barnesiella intestinihominis, Vallitalea pronyensis, Alistipes putredinis, Bacteroides massiliensis, Phocea massiliensis, Kineothrix alysoides, Corynebacterium mastitidis, Lactobacillus reuteri*, and *Bacteroides caecimuris*.

A change in a level of the intestinal microorganism may be identified in a sample isolated from a subject exposed to microplastics compared to a normal control group.

The microplastic exposure may be selected from the group consisting of oral exposure, inhalation exposure, and transdermal exposure.

The brain disease may be induced by ecological changes in intestinal microorganism by microplastic exposure and penetration of microplastics into the brain tissue.

The brain disease may be selected from the group consisting of schizophrenia, frontal lobe epilepsy, autism, and attention deficit hyperactivity disorder (ADHD), more preferably, autism, but is not limited thereto.

The microplastics may be selected from the group consisting of polystyrene, polypropylene, polyethylene, polyamide (PA), acrylonitrile-butadiene-styrene (ABS), polytetrafluoroethylene (PTFE), cellulose acetate (CA), polycarbonate (PC), polymethyl methacrylate (PMMA), polyvinyl chloride (PVC), polyethylene terephthalate (PET), acrylic, melamine resin, and polyurethane (PU).

The microplastics may include harmful substances that are eluted and desorbed from the plastic.

The harmful substance eluted from the plastic may be selected from the group consisting of mineral oil, styrene dimer, trimer perfluorinated compounds, sterilizing preservatives, polyols, acrylates, phenols, melamine, and nitrosamines.

The harmful substance desorbed from the plastic may be selected from the group consisting of heavy metals, sterilizing preservatives, phthalates, bisphenol A, perfluorinated compounds, polychlorinated biphenyls (PCBs), DDTs, hexachlorocyclohexane (HCH), polycyclic aromatic hydrocarbons (PAHs), aliphatic hydrocarbons, nonylphenol, lubricating oil, medicine, carbamazepine (CBZ), 4-methylbenzylidene camphor (4MBC), TriCloSan (TCS), 17$\alpha$-ethinyl estradiol (EE2), sulfadiazine (SDZ), amoxicillin (AMX), tetracycline (TC), ciprofloxacin (CIP), and trimethoprim (TMP).

In addition, the microplastics may include one or more from an additive group to be added to the plastic, consisting of plasticizers, flame retardants, stabilizers antioxidants UV stabilizers, heat stabilizers, slip agents, lubricants, antistatic agents, curing agents, foaming agents, biocides, water-soluble colorants, organic pigments, inorganic pigments, special effect colorants, fillers, and enhancers.

The present disclosure may provide a method for predicting the prognosis of a brain disease induced by microplastic exposure, including obtaining a sample isolated from a subject exposed to microplastics;

identifying whether microbial ecology changes and a change in the metabolite level in the sample; and comparing with a control group.

The sample may be selected from the group consisting of feces, urine, blood, tissues, and cells.

More specifically, whether the microbial ecology changes may be to identify, in the sample, an increase in one or more microorganisms consisting of *Clostridium leptum, Ruminococcus gnavus, Alistipes obesi, Alistipes onderdonkii, Alistipes putredinis, Bacteroides massiliensis, Barnesiella intestinihominis, Blautia faecis, Breznakia pachnodae, Catabacter hongkongensis, Clostridium oryzae, Desulfosporosinus fructosivorans, Desulfovibrio desulfuricans, Gemella palaticanis, Gracilibacter thermotolerans, Kineothrix alysoides, Muribaculum intestinale, Phocea massiliensis, Ruminiclostridium sufflavum*, and *Vallitalea pronyensis*.

In addition, whether the microbial ecology changes may be to identify, in the sample, a decrease in one or more microorganisms consisting of *Bacteroides caecimuris, Lactobacillus reuteri*, and *Corynebacterium mastitidis*.

The change in the metabolite level may be to identify, in the prefrontal cortex tissue sample isolated from the subject, increases in MM09 (macromolecules at 0.9 ppm), MM09+Lip09 (macromolecules and lipids at 0.9 ppm), NAA (N-acetylaspartate) and MM20 (macromolecules at 2.0 ppm); and decreases in Ala (L-alanine) and Ins (myo-inositol).

The change in the metabolite level may be to identify, in a hippocampal tissue sample isolated from the subject, increases in PCr (phosphocreatine) and Lac (L-lactate); and decreases in Ina (myo-inositol), MM09, MM09+Lip09, GABA, Tau (taurine), NAA, and MM20+Lip20 (macromolecules and lipids at 2.0 ppm).

The change in the metabolite may be a decrease in glucose metabolism in the frontal or temporal lobe tissue isolated from the subject.

In addition, the present disclosure may provide a method of providing information for predicting prognosis of a brain disease induced by microplastic exposure, including examining whether microbial ecology changes and a change in a metabolite level from a sample isolated from a specimen.

The term "prognosis" as used herein includes determining whether a subject, in other words, a test subject, will have a disease in the future for a specific disease or disorder, or determining the responsiveness of a test subject to the treatment.

MODES FOR CARRYING OUT THE INVENTION

Hereinafter, to help the understanding of the present disclosure, example embodiments will be described in detail. However, the following example embodiments are merely illustrative of the contents of the present disclosure, and the scope of the present disclosure is not limited to the following examples. The example embodiments of the present disclosure are provided to more completely explain the present disclosure to those of ordinary skill in the art.

<Example 1>Identification of Changes in the Intestinal Microbial Ecology in a Mouse Model by Polyethylene Microspheres Polyethylene (PE) microspheres with a diameter of 10-20 μm were orally administered to BALB/c nude mice everyday by 100 μL at a concentration of 100 ppm for 4 weeks. Thereafter, mouse feces were collected and Illumina 16S Metagenomic Sequencing (MiSeq) was performed over V3 and V4 regions.

As a result, as shown in FIG. 1, significant changes in 23 operational taxonomic units (OTU, reference) were observed in the feces after exposure to PE microspheres. As a result of alpha-diversity analysis, values of the indices (Chaol, Shannon, Simpson) increased significantly, and in the principal component analysis (PCA) among the beta-diversity analysis methods, a significant distinction was detected between the control group and the microbial colonies in the PE microsphere-exposed mouse feces.

In addition, as a result of clustergram analysis, the division between the control group and the PE microsphere-exposed microbial colonies was clearly identified, and as a result of the cladogram analysis, after exposure to PE microspheres at the Class-Order-Family-Genus level, a statistically significant change was observed.

Of 23 OTUs with significant changes observed in the present disclosure, increased were OTUs of *Clostridium leptum, Ruminococcus gnavus, Alistipes obesi, Alistipes onderdonkii, Alistipes putredinis, Bacteroides massiliensis, Barnesiella intestinihominis, Blautia faecis, Breznakia pachnodae, Catabacter hongkongensis, Clostridium oryzae, Desulfosporosinus fructosivorans, Desulfovibrio desulfuricans, Gemella palaticanis, Gracilibacter thermotolerans, Kineothrix alysoides, Muribaculum intestinale, Phocea massiliensis, Ruminiclostridium sufflavum*, and *Vallitalea pronyensis*, whereas 3 OTUs (*Bacteroides caecimuris, Lactobacillus reuteri*, and *Corynebacterium mastitidis*) were decreased.

Thereamong, 13 OTUs (*Breznakia pachnodae, Gracilibacter thermotolerans, Blautia faecis, Desulfosporosinus fructosivorans, Alistipes onderdonkii, Alistipes obesi, Clostridium leptum, Clostridium oryzae, Catabacter hongkongensis, Gemella palaticanis, Ruminiclostridium sufflavum, Desulfovibrio desulfuricans*, and *Ruminococcus gnavus*) were OTPs not identified in the control group, which were found to be newly generated OTPs after PE microsphere exposure.

Of the microorganisms with the change observed, it was found that Lactobacillus reuteri (*L. reuteri*), lactic acid bacteria, rapidly decreased by 0.071 times after PE exposure ($P<0.0128$).

In addition, of the strains with OTU increased, *Alistipes putredinis* and *Barnesiella intestinihominis* were increased by 112.39 ($p=0.00001$) times and 3.89 ($p=0.010$) times respectively, which were also reported to be strains that show high dominance in autistic patients.

<Example 2>Identification of Changes in Metabolic Processes in Polyethylene Microsphere-Exposed Mouse Feces It has been reported that the feces of autistic patients and animal models showed different metabolism from healthy people, and since it is predicted that changes in intestinal microbial diversity may induce changes in metabolic processes as shown in the previous experiment, PICRUSt (phylogenetic investigation of communities by reconstruction of unobserved states, KEGG level 2) analysis was performed using MiSeq data.

Figure 2:
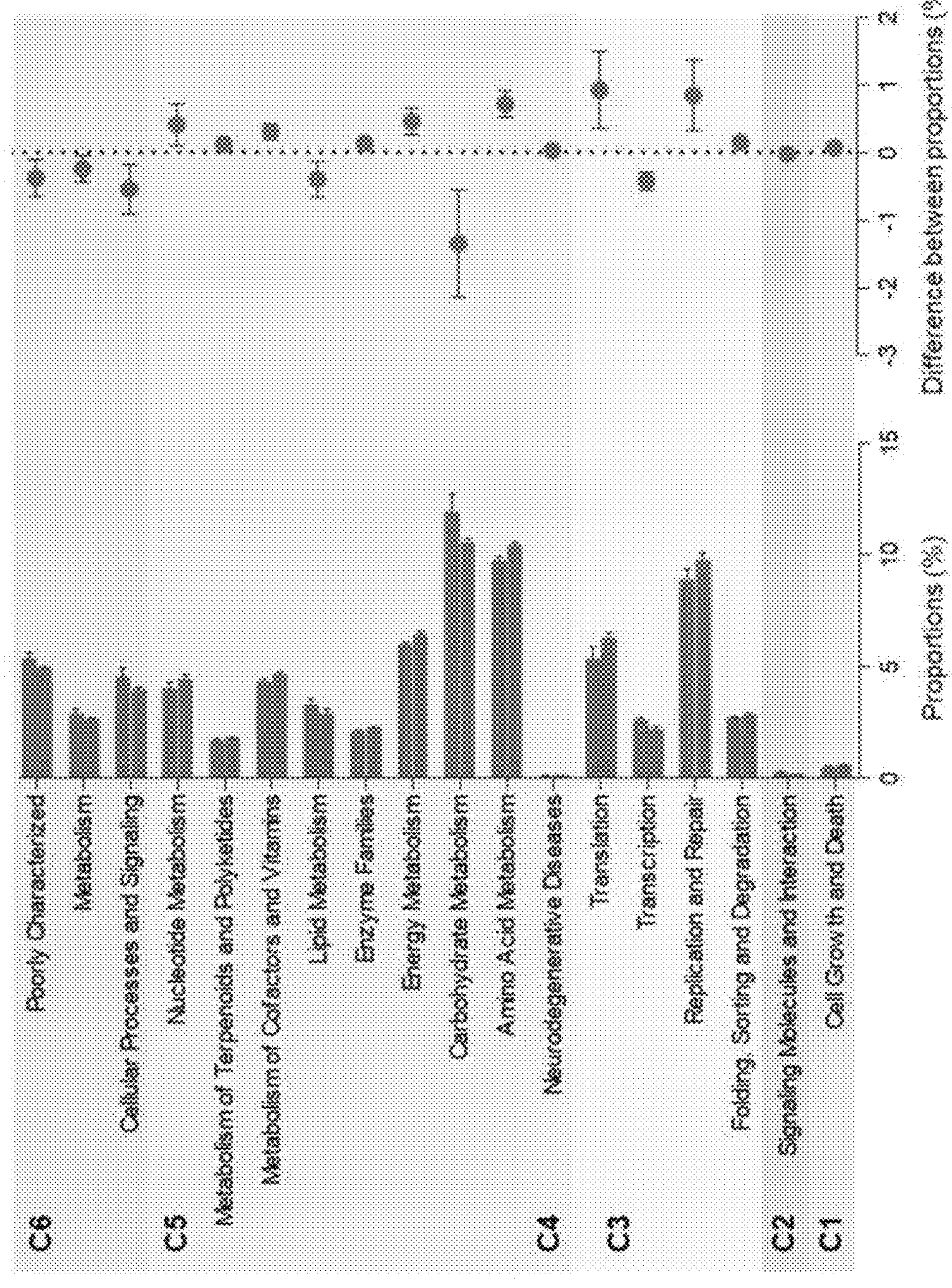
FIG. 2 shows a result of identifying changes in the metabolic process according to the change in the intestinal microbial diversity by performing PICRUSt (phylogenetic investigation of communities by reconstruction of unobserved states) analysis in mouse feces exposed to polyethylene microspheres.

As a result, the functional changes in the metabolism category were observed after PE exposure as shown in FIG. 2. In particular, functional degradation in carbohydrate metabolism and lipid metabolism was observed while functional elevation in nucleotide metabolism and amino acid metabolism was detected.

<Example 3>Identification of Penetration of Polyethylene Microspheres into a Brain Tissue upon Oral Exposure Fluorescent polyethylene (PE) microspheres with a diameter of 10-20 μm were orally administered to BALB/c nude mice by 100 μL, at a concentration of 100 ppm for 4 weeks (100 ppm/100 μL).

After 4 weeks, the mice were euthanized, followed by brain removal of the mice. The brain tissue was physically crushed and dried for a day using a freeze dryer, and the dried tissue was sufficiently dissolved in 70% nitric acid ($HNO_3$) and neutralized using sodium hydroxide (NaOH). After filtering the liquid tissue with a 0.45 um nitrocellulose membrane filter using a vacuum pump, the size and shape of the fluorescent plastic pieces adsorbed onto the filter were observed under a confocal microscope and a scanning electron microscope.

Figure 3:
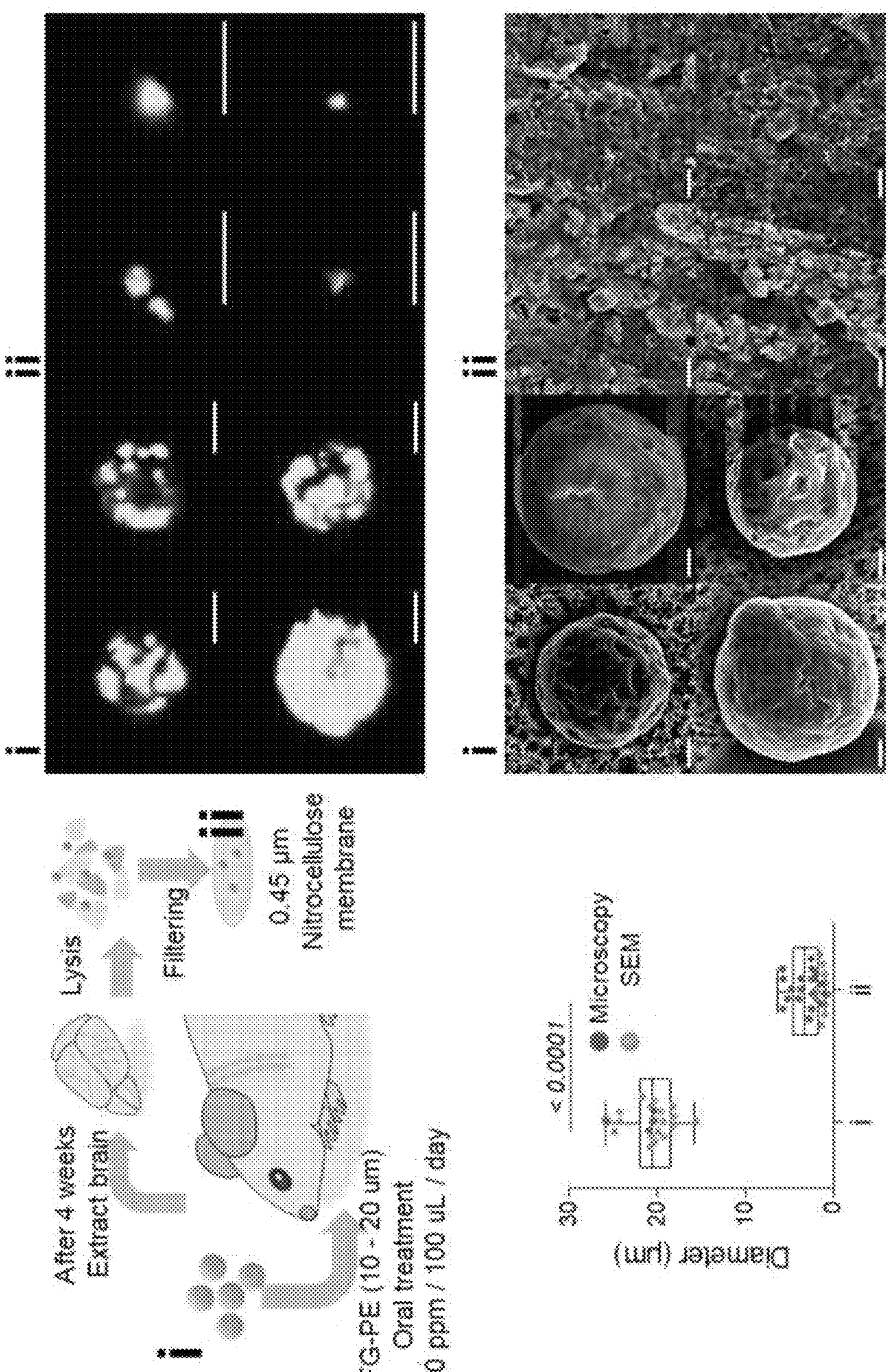
FIG. 3 shows a schematic diagram showing the brain tissue penetration process of orally administered polyethylene microspheres and results of identifying whether polyethylene microspheres penetrate into the brain tissue of a mouse animal model into which polyethylene microspheres are orally administered.

As a result, as shown in FIG. 3, the spherical shape of the PE microspheres was kept intact before administration, but small pieces and irregular shapes were detected on the filter for brain tissue filtration. In addition, the fluorescent PE microspheres were observed to have an average diameter of 20.49 μm before administration, whereas the microplastics adsorbed onto the filter having the brain tissue filtrated were observed to have an average diameter of 3 μm. Such the results are evidence to prove that fragmented microplastics penetrated the brain after undergoing the digestion process in the stomach.

From the above results, it was found that microplastics including PE penetrate the brain, and it may be suggested that such the brain penetration of microplastics had an effect on brain diseases including autism.

<Example 4>Identification of Changes in Brain Metabolites by Polyethylene Microsphere Exposure Fluorescent polyethylene (PE) microspheres with a diameter of 10-20 μm were orally administered to BALB/c nude mice by 100 μL at a concentration of 100 ppm for 1 week (100 ppm/100 μL), and after 1 week, changes in the metabolite were observed in the prefrontal cortex and hippocampus regions of the mice using magnetic resonance spectroscopy (MRS).

Figure 4:
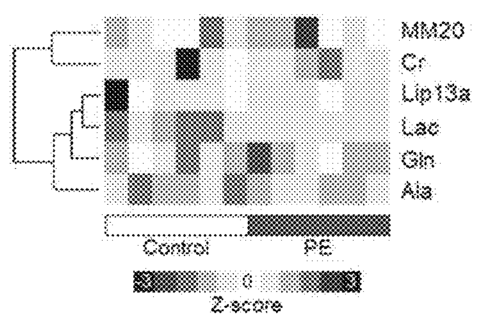
FIG. 4 shows results of identifying changes in the metabolites of the brain tissue of a mouse model into which polyethylene microspheres were orally administered.
Figure 4:
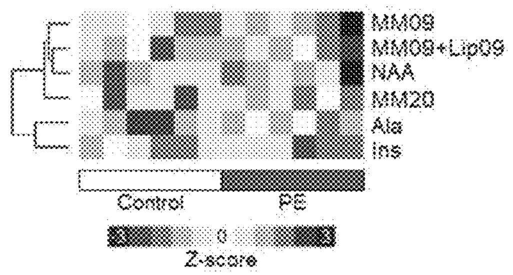
Figure 4:
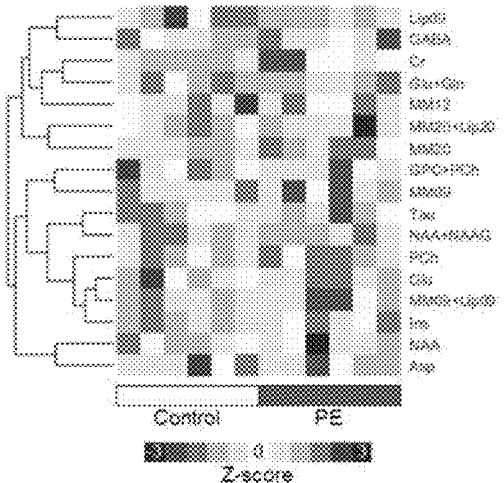
Figure 4:
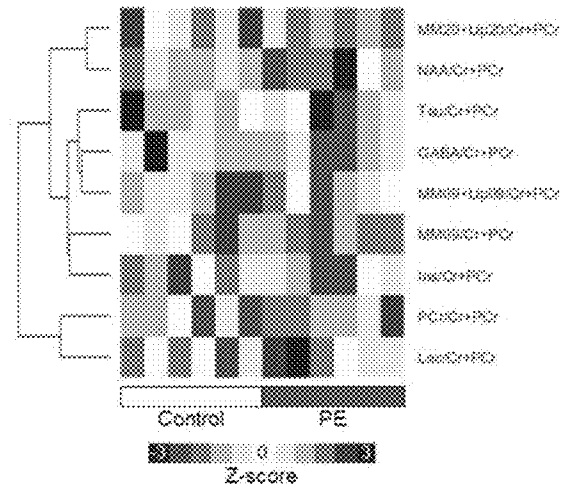

As a result, as shown in FIG. 4, after exposure to PE microspheres, there were increases in the metabolites MM20 and Cr and decreases in Lip13a, Lac, Gln, and Ala in the prefrontal region, and the results that were normalized using Cr+PCr showed increases in MM09, MM09+Lip09, NAA, and MM20 and decreases in Ala and Ins. In the hippocampus region, 17 metabolites including GABA showed a decrease, and a result that was normalized using Cr+PCr showed increases in PCr and Lac and decreases in Ina, MM09, MM09+Lip09, GABA, Tau, NAA, and MM2O+Lip20.

In addition, N-acetylaspartate (NAA) and creatine (Cr) were decreased by 0.64 (p=0.049) and 0.55 (p=0.041) times, respectively, in the hippocampus region.

On the other hand, after exposure to PE microspheres, F-18 fludeoxyglucose (FDG) positron emission tomography (PET) was performed and statistical processing was performed to identify the distribution of glucose metabolism in the brain that showed difference for each region in the mice.

Figure 5:
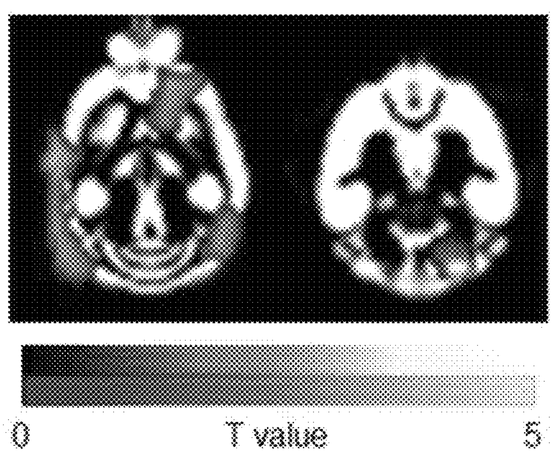
FIG. 5 shows a result of identifying changes in the glucose metabolism for each brain region in a mouse animal model exposed to polyethylene microspheres.

As a result, as shown in FIG. 5, while glucose metabolism was increased in the cerebellum of the mice, that in the frontal lobe and temporal lobe showed a decrease. The decrease in glucose metabolism in the frontal lobe may be interpreted as a decrease in cognition and memory, and such the result was also observed in the Y-maze behavioral experiment that evaluates cognitive function, which is a common outcome of autism symptoms. In addition, compared with normal subjects, it was found that glucose uptake was high in the cerebellum of autistic patients, and an experiment using an autistic mouse model also showed a similar report that had an increase in glucose metabolism in the cerebellum (Sharma, A., et al., World J Nucl Med, 2018. 17(2): p. 94-101.).

<Example 5>Identification of Symptoms of Autism by Polyethylene Microsphere Exposure It was reported that social novelty and interaction were reduced in the autism mouse model, it was found that social interaction was reduced in a mouse model induced with autism by transplanting microorganisms of autistic patients, and it was also observed that social interaction was reduced in various other autism-related mouse models.

Accordingly, fluorescent polyethylene (PE) microspheres with a diameter of 10-20 μm were orally administered to C57BL6 mice by 100 μL at a concentration of 100 ppm for 1 week (100 ppm/100 μL), and to observe whether autism may be induced by PE microsphere exposure, a 3-chamber experiment was performed (change in sociality; Kaidanovich-Beilin, O., et al., Assessment of social interaction behaviors. J Vis Exp, 2011(48)), Y-maze (cognition and obsession; Roullet, F. I. and J. N. Crawley, Mouse models of autism: testing hypotheses about molecular mechanisms. Curr Top Behav Neurosci, 2011. 7: p. 187-212.) and marble-burying behavior study & nestlet shredding test (obsessive-compulsive disorder; Angoa-Perez, M., et al., Marble burying and nestlet shredding as tests of repetitive, compulsive-like behaviors in mice. J Vis Exp, 2013(82): p. 50978.).

Figure 6:
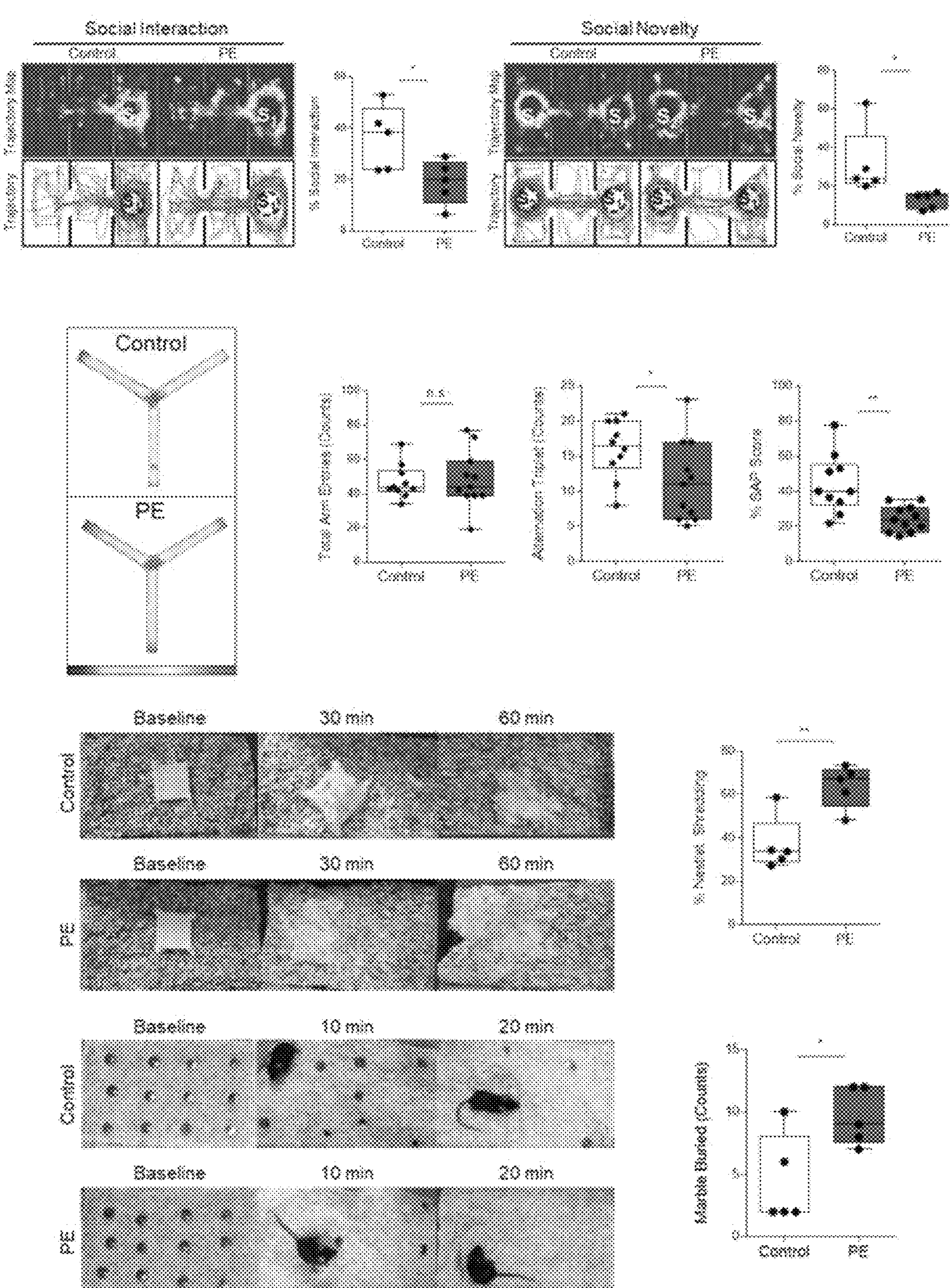
FIG. 6 shows results of performing a 3-chamber experiment (change in sociality), Y-maze (cognition and obsession), marble-burying behavior study (obsessive-compulsive disorder), and nestlet shredding test (obsessive-compulsive disorder) to identify whether autism occurs in a mouse animal model exposed to polyethylene microspheres.

Consequently as shown in FIG. 6, in a result of the 3-chamber experiment, both the social interaction and social novelty of the PE microsphere-exposed mice were reduced compared to the control group. In addition, in the result of Y-maze experiment, the alternation triplet and SAP score were decreased in PE microsphere-exposed mice.

In addition, as a result of the nest building test, higher % nestlet shredding was observed in mice exposed to PE microspheres, and in the marble-burying behavior experiment, the marble-buried rate in mice exposed to PE microspheres was observed higher.

From the above results, it was determined that exposure to microplastics degraded cognitive function and worsened obsessive-compulsive symptoms.

As described above, a specific part of the content of the present disclosure is described in detail, for those of ordinary skill in the art, it is clear that the specific description is only a preferred embodiment, and the scope of the present disclosure is not limited thereby. Accordingly, the substantial scope of the present disclosure may be defined by the appended claims and their equivalents.

The invention claimed is:

1. A method for diagnosing a brain disease induced by microplastic exposure, the method comprising:
- obtaining a feces sample from a human or animal subject that has been exposed to microplastics;
- obtaining a brain tissue sample from a prefrontal cortex or a hippocampus of the subject;
- detecting whether a microbial ecology change is present in the feces sample relative to a feces sample from a normal control subject not exposed to microplastics,
- wherein the microbial ecology change comprises an increase in at least one of *Alistipes putredinis* and *Barnesiella intestinihominis* and a decrease in *Lactobacillus reuteri*;
- detecting whether a metabolite level change is present in the brain tissue sample relative to a brain tissue sample from the normal control subject,
- wherein the metabolite level change comprises a decrease in N-acetylaspartate (NAA) and a decrease in creatine (Cr); and
- diagnosing the subject as having the brain disease induced by the microplastic exposure when the microbial ecology change and the metabolite level change are both detected,
- wherein the brain disease is autism or autism spectrum disorder.

2. The method of claim 1, wherein the brain tissue sample is obtained from the hippocampus of the subject, and the metabolite level change further comprises an increase in phosphocreatine (PCr) and an increase in L-lactate (Lac); and decreases in myo-inositol (Ins), macromolecules detected at 0.9 ppm (MM09), combined macromolecules and lipids detected at 0.9 ppm (MM09+Lip09), gamma-aminobutyric acid (GABA), taurine (Tau), and combined macromolecules and lipids detected at 2.0 ppm (MM20+Lip20).

3. The method of claim 1, wherein the metabolite level change further comprises a decrease in glucose metabolism in a frontal lobe or a temporal lobe tissue of the subject.

4. A method of providing information for diagnosing a brain disease induced by microplastic exposure, the method comprising:
- obtaining a feces sample from a human or animal subject that has been exposed to microplastics;
- obtaining a brain tissue sample from a prefrontal cortex or a hippocampus of the subject;
- examining the feces sample to detect whether a microbial ecology change is present relative to a feces sample from a normal control subject not exposed to microplastics, wherein the microbial ecology change comprises an increase in *Alistipes putredinis* and *Barnesiella intestinihominis* and a decrease in *Lactobacillus reuteri*;

examining the brain tissue sample to detect whether a metabolite level change is present relative to a brain tissue sample from the normal control subject, wherein the metabolite level change comprises a decrease in N-acetylaspartate (NAA) and a decrease in creatine (Cr); and providing information indicating that the subject has the brain disease induced by the microplastic exposure when the microbial ecology change and the metabolite level change are both detected, thereby facilitating the diagnosing of the brain disease.

* * * * *